United States Patent
Van De Vyver

(10) Patent No.: US 11,026,598 B2
(45) Date of Patent: Jun. 8, 2021

(54) ELASTIC MOVEMENT SENSORS AND CALIBRATION

(71) Applicant: BAINISHA CVBA, Lokeren (BE)

(72) Inventor: Patrick Van De Vyver, Lokeren (BE)

(73) Assignee: BAINISHA CVBA, Lokeren (BE)

( * ) Notice: Subject to any disclaimer, the term of this patent is extended or adjusted under 35 U.S.C. 154(b) by 301 days.

(21) Appl. No.: 16/079,648

(22) PCT Filed: Feb. 24, 2017

(86) PCT No.: PCT/EP2017/054424
§ 371 (c)(1),
(2) Date: Aug. 24, 2018

(87) PCT Pub. No.: WO2017/144710
PCT Pub. Date: Aug. 31, 2017

(65) Prior Publication Data
US 2019/0046076 A1 Feb. 14, 2019

(30) Foreign Application Priority Data
Feb. 24, 2016 (EP) .................................... 16157239

(51) Int. Cl.
*A61B 5/11* (2006.01)
*A61B 5/00* (2006.01)

(52) U.S. Cl.
CPC .............. *A61B 5/11* (2013.01); *A61B 5/6804* (2013.01); *A61B 5/6833* (2013.01);
(Continued)

(58) Field of Classification Search
CPC .... A61B 2562/0223; A61B 2562/0261; A61B 2562/12; A61B 2562/18; A61B 34/37; A61B 34/70; A61B 34/71; A61B 5/0002; A61B 5/1038; A61B 5/1107; A61B 5/1121; A61B 5/1122; A61B 5/4023; A61B 5/4519; A61B 5/4566; A61B 5/4571; A61B 5/486; A61B 5/6807; A61B 5/6828; A61B 5/6831; A61B 5/6833; A61B 5/6898;
(Continued)

(56) References Cited

U.S. PATENT DOCUMENTS

| 10,321,827 B2 * | 6/2019 | Kwon .................. A61B 5/0075 |
| 2015/0335288 A1 * | 11/2015 | Toth ..................... A61B 5/6833 |
| | | 600/373 |
| 2016/0038083 A1 | 2/2016 | Ding et al. |

FOREIGN PATENT DOCUMENTS

| BE | 021520 B1 | 12/2015 |
| WO | 2013038214 A2 | 3/2013 |

(Continued)

OTHER PUBLICATIONS

International Search Report from PCT Application No. PCT/EP2017/054424, dated Jun. 14, 2017.

*Primary Examiner* — David J. McCrosky
(74) *Attorney, Agent, or Firm* — Workman Nydegger

(57) ABSTRACT

A sensing system comprises an elastic sensing element for sensing a movement, an inertial measurement system for sensing a movement, and a controller programmed for obtaining movement sensing data from the elastic sensing element and from the inertial measurement system and for calibrating the elastic sensing element using the combined movement sensing data from the elastic sensing element and the inertial measurement system.

20 Claims, 2 Drawing Sheets

(52) U.S. Cl.
CPC ..... *A61B 5/6832* (2013.01); *A61B 2560/0223* (2013.01); *A61B 2560/0247* (2013.01); *A61B 2562/0219* (2013.01); *A61B 2562/164* (2013.01); *A63B 2220/13* (2013.01); *A63B 2220/40* (2013.01); *A63B 2225/50* (2013.01)

(58) Field of Classification Search
CPC ..... A61B 5/725; A61B 5/7267; A61B 5/7405; A61B 5/742; A61B 5/7455; A61B 5/0062; A61B 5/0066; A61B 5/0075; A61B 5/7203; A61B 2505/09; A61B 2560/0223; A61B 2562/164; A61B 34/30; A61B 5/0492; A61B 5/112; A61B 5/1126; A61B 5/6823; A61B 90/30; A61B 90/361; A61B 1/0045; A61B 1/00071; A61B 1/00149; A61B 1/0016; A61B 1/0057; A61B 1/018; A61B 1/05; A61B 2017/00477; A61B 2017/00526; A61B 2034/2048; A61B 2034/2051; A61B 2034/301; A61B 2034/306; A61B 2034/742; A61B 2503/10; A61B 2503/40; A61B 2505/07; A61B 2560/0475; A61B 2562/0219; A61B 5/11; A61B 5/721; A61B 5/7296; A61B 5/6804; A61B 5/6832; A61B 2220/13; A61B 2220/40; A61B 2560/0228; A61B 2560/0238; A61B 2560/0247; G01P 15/00; G01P 15/02; G01P 15/08; G01P 15/12; G01P 15/122; G01P 15/123; G01P 15/125; G01P 15/14; G01P 21/00; G01L 1/14; G01L 1/142; G01L 1/144; G01L 1/146; G01L 1/18; G01L 1/183; G01L 1/20; G01L 1/205; G01L 1/22; G01L 1/2268; G01L 1/2275; G01L 19/02
See application file for complete search history.

(56) References Cited

FOREIGN PATENT DOCUMENTS

| | | |
|---|---|---|
| WO | 2014122041 A1 | 8/2014 |
| WO | 2015061756 A1 | 4/2015 |
| WO | 2016030752 A1 | 6/2016 |

\* cited by examiner

ELASTIC MOVEMENT SENSORS AND CALIBRATION

FIELD OF THE INVENTION

The invention relates to the field of elastic movement sensors. More specifically it relates to a sensor for movement sensing, such as for example a sensor patch, a method for movement sensing and calibration of such sensors.

BACKGROUND OF THE INVENTION

Wearable devices are being widespread through several fields, veterinary, medicine and drug-delivery fields, muscular therapy and sports, rheumatology, etc. One important field where wearable devices could be applied is in the field of measuring movement of an object.

Detection of movement has applications in sports, veterinary, medical applications, etc. Particular examples thereof are analysis of movements in sports and/or analysis of bending of knees or movements of a back during bending, twisting or walking.

The use of inertial movement systems for sensing movement is well known in the art. Nevertheless, these sensor show some limitations.

Recently, the use of elastic sensing elements for detecting movement has been described in international patent application PCT/IB2015/001742, copending herewith.

Nevertheless, there is still room for improvement.

SUMMARY OF THE INVENTION

It is an object of embodiments of the present invention to provide a good motion sensing, whereby accurate measurements can be performed. It is an advantage of embodiments of the present invention that accurate calibration of elastic sensing elements can be performed.

The above object is obtained by a system and method according to the present invention.

The present invention relates to a sensing system comprising an elastic sensing element for sensing a movement, an inertial measurement system for sensing a movement, and a controller programmed for obtaining movement sensing data from the elastic sensing element and from the inertial measurement system and for calibrating the elastic sensing element using the combined movement sensing data from the elastic sensing element and the inertial measurement system. It is an advantage of embodiments of the present invention that the elastic sensing element can be accurately calibrated. It is an advantage that highly accurate measurement data as obtainable with the elastic sensing element can be obtained, due to accurate calibration using an inertial measurement system.

The elastic sensing element for sensing a movement may comprise at least one elastic elongated capacitive or resistive strip or filament.

The elastic sensing element may be a dielectric electro-active polymer strip. It is an advantage of embodiments of the present invention that capacitive measurements can be obtained via elastic elongation, allowing great sensibility, repeatability, chemical and mechanical stability and elastic recovery.

The dielectric electro-active polymer may be any of an electrostrictive polymers or dielectric elastomers.

The flexible sensing element may be a resistive monofilament.

The elastic sensing element may have a stretchability of at least 50% in their length direction.

The system may comprise an elastic patch, the flexible sensing element (101) being embedded in the elastic patch. The elastic patch then may be referred to as elastic sensor patch.

The elastic sensor patch may comprise a flexible substrate to which the flexible sensing element may be attached.

The flexible substrate may be or may comprise an elastic and electrically isolating film layer with a stretchability of at least 100% in all directions in the plane of the film layer (X,Y).

The electrically insulating film may be a stretchable polymer resin film.

The inertial measurement system may comprise an accelerometer.

The inertial measurement system may be embedded in the flexible patch.

The controller may be programmed for triggering a simultaneous measurement by the elastic sensing element and the inertial measurement system.

The controller may be programmed for triggering the simultaneous measurement at first start-up of the sensing system.

The controller may be programmed for deriving calibration data for the elastic sensing element based on a combination of the measurement data obtained during the simultaneous measurement.

The controller may be programmed for deriving calibration data by matching measurement data from the elastic sensing element with measurement data of the inertial measurement system.

The controller may be programmed for deriving calibration data at predetermined time intervals during the lifetime of the sensing system based on a combination of the measurement data obtained during the simultaneous measurement.

In some embodiments, the controller also may be programmed for, in a later phase, using the elastic sensing elements (initially calibrated with the inertial measurement system) for re-calibrating the inertial measurement system or calibrating other inertial measurement systems.

The sensing system furthermore may comprise an output means for providing instructions regarding movements to be performed when deriving calibration data.

The system furthermore may comprise a memory for storing calibration data for the elastic sensing element.

The system furthermore may comprise a communication means for sending data from the elastic sensing element and the inertial measurement system to the controller.

The sensing system may further comprise an adhesive layer for attaching the system to a part of a body.

The controller may be further adapted to transmit measurement data to an output.

The controller may be further adapted to give instructions to the at least one elastic sensing element and/or the inertial measurement system for triggering measurements. It is an advantage of embodiments of the present invention that power may be saved by using the inertial measurement system only when certain conditions are followed.

The flexible patch may comprise the controller. It is an advantage of embodiments of the present invention that the system is compact.

The controller may comprise a wireless signal transmitter and receiver for providing communication between the controller and at least one of the elastic sensing element and/or the inertial measurement system.

The sensing system may further comprise a rechargeable energy source and energy harvesting means, for powering any or all of the elastic sensing element, the inertial measurement system, and the controller.

The patch furthermore may comprise a stretchable transparent electrode.

The stretchable transparent electrode may comprise a thin conductive layer, such as for example a thin conductive layer of carbon nanotubes or any other type of transparent thin conductive layer.

The present invention also relates to a method for calibrating an elastic sensing element, the method comprising sensing of a movement using an elastic sensing element, sensing of a movement using an inertial measurement system, obtaining movement sensing data from said sensing with the elastic an flexible sensing element and from said sensing with the inertial measurement system, and calibrating the elastic sensing element by combining movement sensing data from the elastic sensing element and the inertial measurement system.

Sensing of a movement using an elastic sensing element may comprise measuring at least position, speed or acceleration. In some embodiments, alternatively or in addition thereto also a change in volume or topological dynamics can be measured.

Sensing of a movement using an inertial measurement system may comprise measuring at least position, speed or acceleration using an inertial measurement system.

Calibrating may comprise matching the data obtained by sensing of a movement using an elastic sensing element and the data obtained by sensing of a movement using an inertial measurement system.

The sensing of a movement using an elastic sensing element and using an inertial measurement system may be simultaneously triggered.

The method may further comprise a step of sensing environmental variables for further calibrating the measurements.

The present invention also relates to a processor comprising an algorithm for calibrating a sensing system using a method as described above.

In one aspect, the present invention also relates to a sensing system for sensing movement, the sensing system comprising an elastic sensing element for sensing a movement and an inertial measurement system for sensing a movement. It is an advantage of embodiments of the present invention that particular motions that are difficult to monitor with an inertial measurement system can be measured using the elastic sensing element. Examples of such motions are tiny movements and whip like explosive movements. The system based on elastic sensing element may also be used for comparing similar or identical movements, which is more difficult when using an inertial measurement system. According to embodiments of the present aspect of the invention, optionally, the system also may comprise a controller programmed for obtaining movement sensing data from the elastic sensing element and from the inertial measurement system and for calibrating the elastic sensing element using the combined movement sensing data from the elastic sensing element and the inertial measurement system. Further features and advantages may be as described above for the first aspect.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
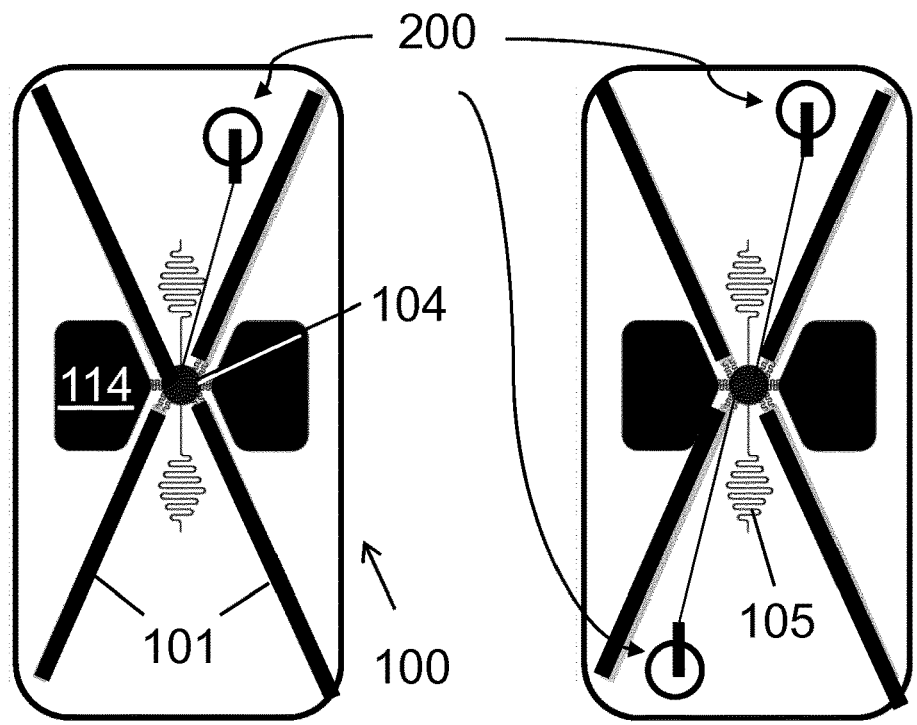
FIG. 1 illustrates two exemplary sensing systems comprising inertial measurement systems, as can be used in embodiments of the present invention.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Where in embodiments of the present invention reference is made to "elastic sensing element", reference is made to a sensor which may change its shape and/or size upon stress, and recover its original shape repeatedly substantially, e.g. 98% of its original form. In embodiments of the present invention, some of its properties (e.g. capacitance, resistivity) change when stress is applied, and the measurable change of property can be correlated to the change of shape and/or size.

Where in embodiments of the present invention reference is made to "inertial measurement system", reference is made to a sensor that gives a measurement signal when movement is sensed, such as an accelerometer, based on inertia. Micro electromechanical systems (MEMS) are an example of such inertial systems.

Where in embodiments of the present invention reference is made to an elastic sensor, reference is made to a sensor that is bendable and stretchable.

Where the present invention refers to "elongation" or "stretching" or "displacement" or "movement", one example may be a movement of a person or animal, e.g. a movement of a joint or the spinal column, and/or the associated stretching of the skin, and/or the associated stretching of the sensing element applied to the skin. This "stretching" of the sensing element may therefore reflect various "underlying" movements, e.g. extension or stretching of a knee or elbow or other joint, bending or stooping or stretching of the back, depending on the place and orientation where the sensor is applied. As indicated above, also a volumetric change or topological dynamics can be used for measuring. The invention therefore is not limited to the measurement of a displacement, movement, elongation or stretching.

In a first aspect, the present invention relates to a sensing system for sensing movement. The sensing system is for example suitable for sensing movement of a human or animal body, for analysing sports movements, etc. embodiments not being limited thereto. The sensing system comprises an elastic sensing element for sensing a movement and an inertial measurement system for sensing a movement. It is an advantage of embodiments of the present invention that particular motions that are difficult to monitor with an inertial measurement system can be measured using the elastic sensing element. Examples of such motions are tiny movements and whip like explosive movements. The system based on elastic sensing element may also be used for comparing similar or identical movements, which is more difficult when using an inertial measurement system.

The elastic sensing element may be embedded in or positioned on an elastic layer with a certain degree of stretchability, for example, at least 100%, in width and length (in all directions of the plane of the film layer) as a substrate for at least one elastic sensing element. The elastic sensing element thus may be implemented as an elastic patch, e.g. an elastic patch according to an embodiment as described in international patent application PCT/IB2015/001742, although embodiments of the present invention are not limited thereto.

A suitable example of elastic sensing element may comprise materials whose electric characteristics change when submitted to strain. The stretching of the elastic element may provide a resistive and/or capacitive change. A suitable material for an elastic sensing element may be a filament or a fibre thereof. It may be a thermoplastic elastomer with a resistivity which changes as a function of the length of the filament or fibre. A preferred elastic sensing element may additionally or alternatively comprise an elastic strip attached to the elastic dielectric layer, wherein the strip comprises a capacitive strip with a dielectric electro-active polymer and has a stretchability of at least 50% in its length direction.

The strip may comprise a part of the elastic material sandwiched between two conductive layers, thereby providing capacitive change upon change of layer thickness when stretching the elastic material. In some embodiments of the present invention, the sensing element may be as described in international patent application PCT/IB2015/001742.

In some embodiments of the present invention, the elastic sensing element is embedded in an elastic patch. In other specific embodiments of the present invention, the sensor system concerns a sock, collar or sleeve, shirt or in general a garment to be placed over a limb of a person or animal, wherein the garment is typically made of an elastic material such as for example a textile or a textile-like material or an elastomer material. When embedding or attaching the sensor to the elastic garment, it is not necessary for an elastic and electrically isolating film layer to be present, such as is present for embodiments of the conventional form of a patch. In some examples the sensor may be intertwined with the elastic material, e.g. the textile or textile-like material, or it may for example be connected to the garment at its end or at the ends and at some intermediate points.

Embodiments of the invention further comprise at least one inertial measurement system which may obtain dynamic information regarding the position, speed and acceleration of the element, body or alike that is studied. The inertial system may be for example attached to the part of the body under study, may be embedded in an object or a textile, etc. and may in other embodiments even be comprised in an elastic sensor patch comprising the elastic sensing element. The system may take measurements continuously, or in preferred embodiments, only at predetermined times. Embodiments of the elastic sensing system of the present invention further comprise at least one inertial measurement system, for example at least one of, or a combination of, accelerometers, piezoelectric accelerometers, a piezoresistive or capacitive MEMS, etc.

In some embodiments, both the elastic sensing element and the inertial measurement system are embedded or attached in a patch or garment. Embedding or attaching as stated above may take place in any manner whatsoever. The garment may be provided with an adhesive edge on the top and/or underside, which can counter the slipping of the garment after it has been positioned.

According to embodiments of the present aspect of the invention, optionally, the system also may comprise a controller programmed for obtaining movement sensing data from the elastic sensing element and from the inertial measurement system and for calibrating the elastic sensing element using the combined movement sensing data from the elastic sensing element and the inertial measurement system. Such a controller may comprise for example a processor or microprocessor for processing measurement data. Such a controller also may comprise a memory for storing data, such as for example calibration data.

The controller may comprise an algorithm for controlling the system such that it is adapted for taking a measurement using the inertial measurement system at the start up, or a measurement when a condition (e.g. certain speed) is reached, or a periodic measurement. In this case, the measurement frequency used for the inertial measurements may be lower than the measurement frequency of the sensing elements, since a single or regularly calibration process may be sufficient and there may be no need to calibrate for every single measurement.

The controller may be programmed for automatically triggering a calibration, e.g. when the system is first used, at predetermined moments in time, etc.

Additionally, the controller may also trigger the measurements by the inertial measurement system. For example, in case the speed or type of movement is such that the sensibility of the elastic sensing element is badly affected, the inertial measurement system can be used for taking measurements, or for calibration. The controller may also trigger the inertial measurement system periodically. The measurement frequency may be very high, for example hundreds of measurements may be obtained per second, improving the precision in dynamic conditions. In additional or alternative embodiments, the controller may comprise an algorithm which triggers the measurement of the inertial measurement system and/or of the sensing strip when certain conditions take place. For example, it may trigger the measurements periodically or depending on the speed of the movement, which may be directly obtained with the inertial system In some embodiments, the sensing system may also comprise an integrated circuit and electrically connected with the flexible sensing element. The connections may be made by means of elastic electric connections such as conductive paste, stretchable electronic leads, or the like. The integrated circuit may comprise a programmable processor. The program may be stored in non-volatile memory (e.g. embedded flash) or may be hard-coded. The integrated circuit may not need be elastic, but may be flexible. It may comprise peripheral components (e.g. resistors, capacitors, a clock module and similar) as known in the prior art. In some embodiments, substrates may also be provided with an integrated circuit which is both bendable and stretchable.

FIG. 1 shows two exemplary embodiments of the present invention comprising an inertial measurement system 200 and a patch 100. The configuration on the left side comprises a single MEMS, and the configuration on the right side comprises a couple of MEMS embedded in the patch 100, in opposite extremes of the patch. Instead of MEMS, other inertial accelerometers (piezoelectric accelerometers, etc) may be used, in so far as their size and shape allows embedding in the patch. In some embodiments, the inertial system may be placed outside the patch. The particular embodiment of FIG. 1 shows a cross-configuration of the sensing strips 101. The integrated circuit 104 may receive the data from the strips 101 and from the inertial measurement systems 200 via an elastic conductor, or via a wireless antenna 105, which is advantageous in those embodiments in which the inertial systems are distant from the patch (not embedded therein). An energy source 114, such as a flexible and/or elastic battery, may be provided to power the sensors. The energy source may be rechargeable, and it may comprise energy harvesting means. For instance, the antenna may be also used for wireless recharging using RF signals or similar.

Figure 2:
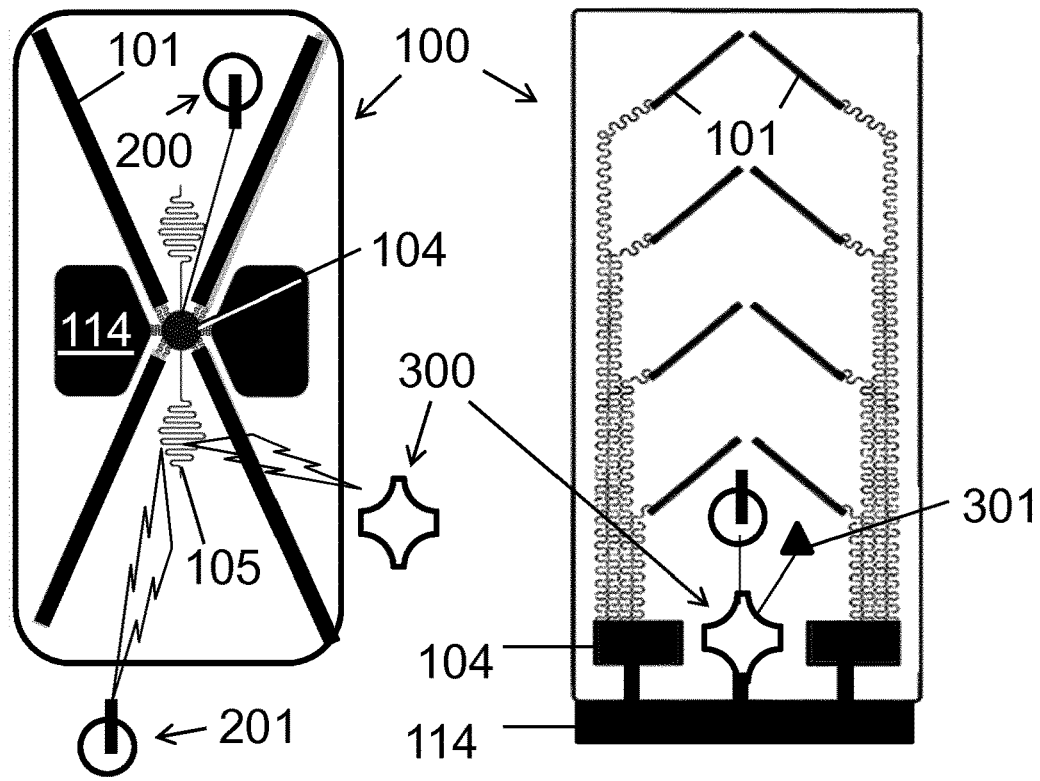
FIG. 2 illustrates two exemplary sensing systems of the present invention, with a controller distant from a sensing patch (left image) and a controller included in a sensing patch (right image).

FIG. 2 shows two possible configurations of a controller 300. It may be distant from the patch 100, as shown in the embodiment on the left of FIG. 2, or it may be included in the patch 100 as shown in the configuration on the right of FIG. 2. For example it may be part of, or connected to, the integrated circuit 104.

In order to power the sensing element, the inertial measurement system and any other power-consuming element in the measurement system, such as the controller or any integrated circuit, an energy source may be included. For example, the energy source may be a rechargeable battery. In advantageous embodiments, a flexible and stretchable battery may be used, as known in the art. The sensor patch may furthermore comprise a charging circuit with wireless charging of the rechargeable energy source. Additionally or alternatively, energy harvesting may be provided, for example an ambient backscatter system which converts ambient radiation into energy, a system that converts movement or vibration to energy, a thermoelectric converter, or a system which uses an electrochemical process to convert perspiration into energy. Systems like energy harvesting and wireless charging provide longer autonomy to the sensing system. This increases the autonomy of the system.

The sensing system, in one example, may furthermore comprise other sensors which obtain information of environmental factors. For example, a temperature sensor may be provided and the integrated circuit may be provided with an algorithm for storing the measured temperature in the memory, and/or for compensating the measurement values taking into account the temperature measured. It is an advantage for the sensing system to have a temperature sensor and a temperature compensation algorithm because this allows an improvement in the precision of the measurement values. For example, the algorithm in the controller may include a condition in which calibration takes place when certain conditions of temperature and/or humidity are detected, in order to compensate for any influence of these factors.

In some embodiments of the present invention a controller and wired sensor may be combined. The controller may be a compact self-adhesive controller. In one embodiment, the system comprises printed batteries, stretchable micro-leads connecting a MEMS-IMU and a microprocessor, a printed antenna connected with the micro-processor, a micro-processor, a 6-DOF MEMS-IMU package and a folding line. The device may be a patch, the patch may combine the device, with a device fixation adhesive, a substrate, a long-term wear adhesive and a release liner.

In a second aspect, the present invention relates to a method of movement sensing and/or to a method for calibrating an elastic sensing element. In the method of movement sensing, the method comprises sensing a movement using an elastic sensing element and sensing a movement using an inertial measurement system. The elastic sensing element may be as described in the first aspect. The inertial measurement system also may be as described in the first aspect.

In one set of embodiments, the sensing using two different types of sensing elements provides the advantage that for example movements that can be only measured in a limited way using an inertial measurements system, can now be more accurately measured by combining the inertial measurements with measurements using the elastic sensing element. Examples of such movements are tiny movements, comparison of similar or identical movement and whip-like explosive movements.

In another set of embodiments, the sensing of the movement using both an elastic sensing element and an inertial measurement system may alternatively or in addition be used for calibrating. The method then may further comprise obtaining movement sensing data from said sensing with the elastic an flexible sensing element and from said sensing with the inertial measurement system, and calibrating the elastic sensing element by combining movement sensing data from the elastic sensing element and the inertial measurement system. Sensing of a movement using an elastic sensing element and sensing of a movement using an inertial measurement system may comprise measuring at least position, speed or acceleration. The calibrating may comprise matching the data obtained by sensing of a movement using an elastic sensing element and the data obtained by sensing of a movement using an inertial measurement system. Calibration may include simultaneously triggering of the sensing of a movement using an elastic sensing element and the sensing of a movement using an inertial measurement system. For the calibration, also other environmental variables could be taken into account.

Sensing a movement may in some example comprise retrieving data using an elastic sensing element on an elastic material (forming a patch or garment). For example at least one capacitor or resistor whose capacitance or resistance change with strain may be embedded in the elastic material.

A calibration step may in some example comprise obtaining a measurement using accelerometers or any other inertial measurement system attached to the same area in which the elastic material is applied, for example the inertial system may be also embedded in the elastic material. The combination of the two types of measurements can be used to calibrate the results, e.g. the results from the elastic sensing element, and they may be send to an output. This calibration may be done by data comparison, weighting, correction, compensation or any other suitable way.

The different method steps may be performed or controlled by a controller, such as a microcontroller, microprocessor or the like. The calibration data may be sent to the elastic sensing element, stored in a memory or alike. Communication between the elastic sensing system, the inertial system and the processor may be wired or wirelessly.

A step of energy harvesting may be included, for powering the sensing elements and/or the processor, or for recharging a battery such as an elastic battery.

Data transmission may be done wirelessly. For example, the processor may be wearable comprising a digital display connected to the patch and/or inertial measurements via Bluetooth, capacitive or RF connection.

Further optional steps may comprise sensing environmental factors and sending them to the controller. An integrated circuit or controller may comprise a temperature and/or humidity sensor and the necessary software for the processor to take account of the dependency with these factors (e.g. by means of a reference table or a mathematical formula).

Figure 3:
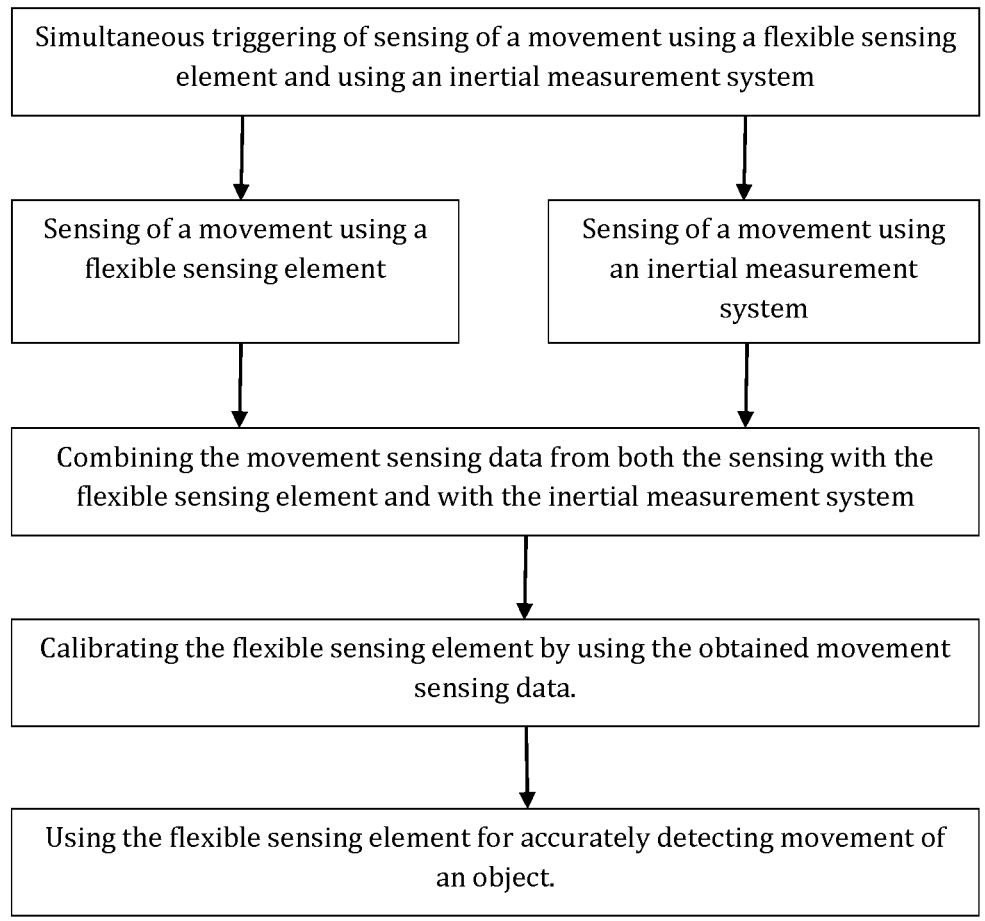
FIG. 3 shows a flowchart of the method according to embodiments of the present invention.

An example of possible steps is shown in FIG. 3.

In a further aspect of the present invention, a processor comprising an algorithm for carrying out any or all of the steps described with respect to the second aspect of the present invention is provided.

Embodiments of the present invention may be used for a plurality of applications. A non-limiting list of applications wherein sensors according to embodiments of the present invention can be used are those applications as described in international patent application PCT/IB2015/001742, incorporated herein completely by reference. Examples of applications are measurements of movements of the human or animal body, arthroplasty, detection of reduced coordination, early detection of neurodegenerative diseases, detection or monitoring of movements of training materials, such as a training ball, smart sensors in textiles, etc. These uses are advantageously improved by the in-situ calibration that the system provides.

By way of illustration, embodiments of the present invention not being limited thereto, a particular example comprises obtaining measurements of movements of e.g. a cyclist, using a particular CFD module and calculating in real-time the air resistance of a cyclist on his bike. The latter can also be used, with different models, for other types of sports, movements or activities. In one particular example, real-time information can be obtained for deciding how the drag on a racer can be minimized (the information can e.g. be provided via smart goggles). The information is deduced for example from an advanced combination of ultra fast computational fluid dynamics and a set of textile integrated sensors which dynamically measure the posture of the cyclist. The technique is based on a library based closest fit CFD model selection that links with a real-life High Definition Human Body Motion Capturing. Aerodynamic testing is not required, but can be used if results are available. The system can operate based on a 3D-photo of the racer. Optionally, also extra data or drag data can be used, such as for example the type of bicycle, wheels, suit texture, etc. In some embodiments, also other riders in a tight knit group and their influence can be taken into account. In a corresponding method, the method may comprise taking a 3D image, e.g. a snapshot of cyclist wearing gear, may comprise collect relevant CFD-models from a library and link it to a wire-frame, may comprise linking of the wire-frame to measurement devices and may comprise projecting the results in real-time during e.g. a race.

By way of illustration, embodiments of the invention not being limited thereto, an example of a kit of parts is described below. The kit of parts in some embodiments may be a generic test kit comprising an elastic sensing element for sensing a movement, an inertial measurement system for sensing a movement, and a controller programmed for obtaining movement sensing data from the elastic sensing element and from the inertial measurement system and for calibrating the elastic sensing element using the combined movement sensing data from the elastic sensing element and the inertial measurement system. The inertial measurement system may be incorporated in the controller.

In one exemplary embodiment, the elastic sensing element may be a single-use self adhesive sensor, which may be coupled to one or more button sized controllers. The system also may comprise a complementary set of single-use sensors. The sensors may be 100% stretchable for endless life. The accuracy may be for example at least 0.2% of the displacement. The sensing speed of the sensors may be up to 1000 Hz. In the exemplary embodiment, the controller may comprise for example a $3^{rd}$ generation 9 DOF MEMS-IMU sensing device. Data transmission may be based on powerful wireless transmission. Charging may be performed on any type of technologies, in one example being based on wireless chargeable batteries. The kit of parts may for example also comprise a charging station. The controller also may comprise a processing unit for processing data from the polymer sensors. According to some embodiments, the kit also may comprise one or more of a compression sleeve, straps, a manual and main site access CD. Suitable basic software may be downloadable. The stretchable sensors provided may be general purpose stretchable sensors, but may alternatively also be adapted for specific applications.

In one example, the stretchable sensor may be a band sensor that can be placed on the forearm.

In yet another example, an application for the knee is envisaged whereby an upper and lower MEMS-IMU sensor is provided in combination with a polymer sensor, such as a multi-directional polymer displacement sensor, e.g. an X-shaped sensor configuration. The X-shaped sensor typically comprises replaceable textile-adhesive sensor patches in X-configuration which allows to provide information on the knee instability and provide high-definition information regarding the joint dynamics. The X-shaped sensor configuration may comprise a central processor and a transmitter. The kit allows to obtain spatial 3D data of upper/lower limb and allows automatic calibration of the knee angle. The kit may comprise a controller for wireless data transmission capability. In some examples the sensors can be provided on a tight fit textile substrate, or the kit of parts may comprise such a tight fit textile substrate, e.g. a stocking or knee brace.

In some embodiments, the kit of parts may comprise a controller which allows RF wireless data transfer. The controller may for example comprise an RF transmitter, a battery and a signal processor. Transmission may for example be performed to a processing computer, and the kit of parts may comprise an RF receiver that can be coupled to the processing computer. In some embodiments, the connection between the flexible sensor and the controller may be wireless or wired. In some applications, the sensed movement can be imaged on a screen, e.g. a bill board screen.

The kit of parts may be adjusted such that a sensor suitable for sensing the back of a person is present in the kit of parts.

The kit of parts also may comprise other components.

The invention claimed is:
1. A sensing system comprising:
an elastic sensor configured to sense a movement,
an inertial measurement system for sensing a movement,
a controller programmed for obtaining movement sensing data from the elastic sensor and from the inertial measurement system and for calibrating the elastic sensor using the combined movement sensing data from the elastic sensor and the inertial measurement system,
wherein the controller is programmed to trigger a simultaneous measurement to obtain measurement data by the elastic sensor and the inertial measurement system and to derive calibration data for the elastic sensor based on a combination of the measurement data obtained during the simultaneous measurement, and
wherein the controller is programmed to, in a later phase, use the elastic sensor for re-calibrating the inertial measurement system or calibrating other inertial measurement systems.

2. A sensing system according to claim 1, wherein the elastic sensor comprises one or more of:
an elastic elongated capacitive strip,
an elastic elongated capacitive filament,
an elastic elongated resistive strip,
elastic elongated filament,
a dielectric electro-active polymer strip,
a dielectric electrostrictive polymer, and
a dielectric elastomer or a resistive monofilament.

3. A sensing system according to claim 1, wherein the elastic sensor has a stretchability of at least 50% in its length direction.

4. A sensing system according to claim 1, wherein the system comprises an elastic sensor patch, the elastic sensor being embedded in the elastic sensor patch or
wherein the system comprises an elastic sensor patch comprising a flexible substrate to which the flexible sensor is attached.

5. A sensing system according to claim 4, wherein the flexible substrate is or comprises an elastic and electrically isolating film layer with a stretchability of at least 100% in all directions in the plane of the film layer (X,Y) or
wherein the flexible substrate is or comprises an elastic and electrically isolating stretchable polymer resin film layer with a stretchability of at least 100% in all directions in the plane of the film layer (X,Y).

6. A sensing system according to claim 4, wherein the inertial measurement system also is embedded in the elastic sensor patch.

7. A sensing system according to claim 4, wherein the elastic sensor patch comprises:
the controller, or a stretchable transparent electrode, or
a stretchable transparent electrode comprising a thin conductive layer of carbon nanotubes.

8. A sensing system according to claim 1, wherein the inertial measurement system comprises an accelerometer.

9. A sensing system according to claim 1, wherein the controller is programmed to trigger a simultaneous measurement at the first start-up of the sensing system.

10. A sensing system according to claim 9, wherein the controller is programmed to derive calibration data by matching measurement data from the elastic sensor with measurement data of the inertial measurement system or is programmed for deriving calibration data at predetermined time intervals during the lifetime of the sensing system based on a combination of the measurement data obtained during the simultaneous measurement.

11. A sensing system according to claim 1, wherein the sensing system furthermore comprises an output means for providing instructions regarding movements to be performed when deriving calibration data.

12. A sensing system according to claim 1, wherein the system furthermore comprises a memory for storing calibration data for the elastic sensor.

13. A sensing system according to claim 1, wherein the system furthermore comprises a communication means for sending data from the elastic sensor and the inertial measurement system to the controller or wherein the system further comprises a rechargeable energy source and energy harvesting means, for powering any or all of the elastic sensor, the inertial measurement system, and the controller.

14. A sensing system according to claim 1 wherein the sensing system further comprises an adhesive layer for attaching the system to a part of a body.

15. A sensing system according to claim 1, wherein the controller is further adapted to transmit measurement data to an output or wherein the controller is further adapted to give instructions to the at least one elastic sensor and/or the inertial measurement system for triggering measurements or wherein the controller comprises a wireless signal transmitter and receiver for providing communication between the controller and at least one of the elastic sensor and/or the inertial measurement system.

16. A sensing system according to claim 1, wherein the sensing system is provided as a kit of parts.

17. A method for calibrating an elastic sensor, the method comprising:
   sensing of a movement using an elastic sensor,
   sensing of a movement using an inertial measurement system,
   obtaining movement sensing data from said sensing with the elastic an flexible sensor and from said sensing with the inertial measurement system, and
   calibrating the elastic sensor by combining movement sensing data from the elastic sensor and the inertial measurement system, and
   using the elastic sensor for re-calibrating the inertial measurement system or calibrating other inertial measurement systems.

18. A method according to claim 17, wherein sensing of a movement using an elastic sensor comprises measuring at least position, speed or acceleration, or
   wherein sensing of a movement using an inertial measurement system comprises measuring at least position, speed or acceleration using an inertial measurement system, or
   wherein the sensing of a movement using an elastic sensor and using an inertial measurement system are simultaneously triggered.

19. A method according to claim 17, wherein calibrating comprises matching the data obtained by sensing of a movement using an elastic sensor and the data obtained by sensing of a movement using an inertial measurement system or wherein the method furthermore comprises a step of sensing environmental variables for further calibrating the measurements.

20. A processor comprising an algorithm for calibrating a sensing system using a method according to claim 17.

* * * * *